US012797332B2

(12) United States Patent
Haeusler et al.

(10) Patent No.: US 12,797,332 B2
(45) Date of Patent: Nov. 17, 2026

(54) USE OF SODIUM OCTENYL-SUCCINATE STARCHES AS A BINDER IN CONTINUOUS WET GRANULATION

(71) Applicant: ROQUETTE FRERES, Lestrem (FR)

(72) Inventors: Olaf Haeusler, Fletre (FR); Lise Vandevivere, Merelbeke (BE)

(73) Assignee: Roquette Freres, Lestrem (FR)

( * ) Notice: Subject to any disclaimer, the term of this patent is extended or adjusted under 35 U.S.C. 154(b) by 1127 days.

(21) Appl. No.: 17/755,756

(22) PCT Filed: Nov. 6, 2020

(86) PCT No.: PCT/EP2020/081387

§ 371 (c)(1),
(2) Date: May 6, 2022

(87) PCT Pub. No.: WO2021/089848

PCT Pub. Date: May 14, 2021

(65) Prior Publication Data

US 2022/0387322 A1 Dec. 8, 2022

(30) Foreign Application Priority Data

Nov. 8, 2019 (EP) .................................... 19306456

(51) Int. Cl.
*A61K 9/16* (2006.01)
*A61K 9/20* (2006.01)

(52) U.S. Cl.
CPC .......... *A61K 9/1652* (2013.01); *A61K 9/2059* (2013.01)

(58) Field of Classification Search
None
See application file for complete search history.

(56) References Cited

U.S. PATENT DOCUMENTS

2016/0354316 A1 12/2016 Swinney et al.

FOREIGN PATENT DOCUMENTS

| | | | | | |
|---|---|---|---|---|---|
| CN | 102671200 | A | | 9/2012 | |
| CN | 104086661 | A | | 10/2014 | |
| CN | 105146513 | A | | 12/2015 | |
| CN | 106538811 | A | | 3/2017 | |
| CN | 108409872 | A | | 8/2018 | |
| EP | 0499648 | A1 | | 8/1992 | |
| WO | WO-0189679 | A2 | * | 11/2001 | ................ A61J 3/02 |
| WO | WO-2005099674 | A1 | * | 10/2005 | ............. A61K 47/36 |
| WO | 2015/073231 | A1 | | 5/2015 | |
| WO | WO-2019014121 | A1 | * | 1/2019 | ............. A61K 47/36 |

OTHER PUBLICATIONS

Wang et al., "Chinese Medicine Quality Derived From Design Methods and Applications for-( VI) : Continuous Manufacturing," World Chin Med 2018; 13(3):566-573. (The English abstract included).

* cited by examiner

*Primary Examiner* — Tigabu Kassa

(57) ABSTRACT

The present invention relates to the use of sodium octenyl succinate starch as a binder in twin screw granulation, in particular for pharmaceutical solid dosage form and the granule obtainable by the method thereof.

11 Claims, 3 Drawing Sheets

USE OF SODIUM OCTENYL-SUCCINATE STARCHES AS A BINDER IN CONTINUOUS WET GRANULATION

TECHNICAL FIELD

The present invention relates to the use of octenyl succinate starch, in particular sodium octenyl succinate starch as a binder in continuous wet granulation, in particular for pharmaceutical solid dosage form and the granule obtainable by the method thereof.

BACKGROUND ART

Wet granulation is widely used in the pharmaceutical industry due to its versatility and reliability in achieving the desire granule properties. Wet granulation can be applied to all drugs and is considered as a universal way to produce tablets.

Wet granulation is a process in which powders are agglomerated by adding a granulating liquid to form granules. Wet granulation improves flow, compactibility to form tablets, content uniformity, generates uniform particle size and shape, and minimizes the impact of minor changes in drug substance and excipient properties.

Wet granulation was originally practiced in a batch process as a low-shear technique or with fluid bed granulation. Then a high-shear process was introduced and made wet granulation a continuous technique which is much faster and more efficient.

Research was needed to fully understand the continuous twin-screw granulation process, especially the relationship between formulation and process parameters affecting the granule attributes before the technology could be applied at industrial scale. The major focus of research on continuous twin screw wet granulation has been on the evaluation of different process parameters. Nevertheless, the type of binder may also have a major influence on the properties of granules and on the product quality of the tablets such as the friability. Therefore, a wide screening of different binders during formulation development is essential. Thus, it remains a need to identify good binders which are suitable to be used in a continuous wet granulation process.

SUMMARY OF THE INVENTION

The inventors studied the effect of different binder types on the properties of granules produced via continuous wet granulation. They demonstrated that a lower amount of granulation liquid is required to obtain good granule quality (granule friability and size) when sodium octenyl succinate starch is used as binder. This behavior can be explained by the wetting properties of the binder. The need of lower amount of granulation liquid is beneficial for a faster drying process of the granules and the quality of the granules.

In a first embodiment, the invention relates to a method for preparing granules comprising one or several substances by continuous wet granulation comprising the step of: a) feeding substance powder to a continuous wet granulator, b) feeding a granulation liquid to said continuous wet granulator, c) wetting the substance powder with the granulation liquid in presence of a binder consisting of an octenyl succinate starch in order to obtain granules and d) drying said granules. Said continuous wet granulation is preferably extrusion granulation, more preferably twin screw granulation. In a particular embodiment, the method comprises the steps of a1) mixing substance powder with powder of said binder, a2) feeding said powder mixture to a continuous wet granulator, b) feeding a granulation liquid consisting of a solvent to said continuous wet granulator, c) wetting the powder mixture with the solvent in order to obtain said granules, d) drying said granules. In another particular embodiment, the method comprises the steps of a) feeding said substance powder to a continuous wet granulator, b) feeding a granulation liquid comprising said binder to said continuous wet granulator, c) wetting the substance powder with the granulation liquid in order to obtain said granules, d) drying said granules. Preferably, the method as previously described further comprises a step e) of milling the dried granules. In a preferred embodiment, said octenyl succinate has a weight average molecular weight comprised between $10^4$ and $10^7$ g/mol, preferably $10^4$ and $10^6$ g/mol, more preferably $10^5$ and $10^6$ g/mol. In a first preferred embodiment, the octenyl succinate has a weight average molecular weight of between 100 000 and 500 000 g/mol, preferably 100 000 and 400 000 g/mol, still preferably 100 000 and 300 000 g/mol, still preferably 100 000 and 200 000 g/mol, still again more preferably 150 000 g/mol. In another preferred embodiment, said octenyl succinate has a weight average molecular weight comprised between 300 000 and $10^6$ g/mol, more preferably 400 000 to 900 000 g/mol, still preferably 500 000 to 800 000 g/mol, still preferably 550 000 to 750 000 g/mol, more preferably 600 000 g/mol. In another preferred embodiment, said octenyl succinate starch is a waxy maize octenyl succinate starch. Said octenyl succinate starch content is preferably between 1 and 50%, preferably 1 and 15% by weight of the total dry weight of said granules. In a preferred embodiment said substance is a pharmaceutical active agent.

In another embodiment, the present disclosure relates to a method for preparing pharmaceutical tablets comprising the steps of preparing granules as previously disclosed and a final step of compressing the granules in order to obtain tablets.

The present disclosure also relates to a granule comprising one or several substances and an octenyl succinate starch having a weight average molecular weight comprised between $10^4$ and $10^7$ g/mol, preferably $10^4$ and $10^6$ g/mol, more preferably $10^5$ and $10^6$ g/mol and to a pharmaceutical tablet comprising said granule. In a first preferred embodiment, said octenyl succinate has a weight average molecular weight of between 100 000 and 500 000 g/mol, preferably 100 000 and 400 000 g/mol, still preferably 100 000 and 300 000 g/mol, still preferably 100 000 and 200 000 g/mol, still again more preferably 150 000 g/mol. In another preferred embodiment, said octenyl succinate has a weight average molecular weight comprised between 300 000 and $10^6$ g/mol, more preferably 400 000 to 900 000 g/mol, still preferably 500 000 to 800 000 g/mol, still preferably 550 000 to 750 000 g/mol, more preferably 600 000 g/mol.

In another aspect, the present disclosure relates to the use of octenyl succinate starch as a binder for continuous wet granulation.

BRIEF DESCRIPTION OF THE DRAWINGS

Other features, details and advantages will be shown in the following detailed description and on the figures, on which.

DETAILED DESCRIPTION OF THE INVENTION

Figure 1:
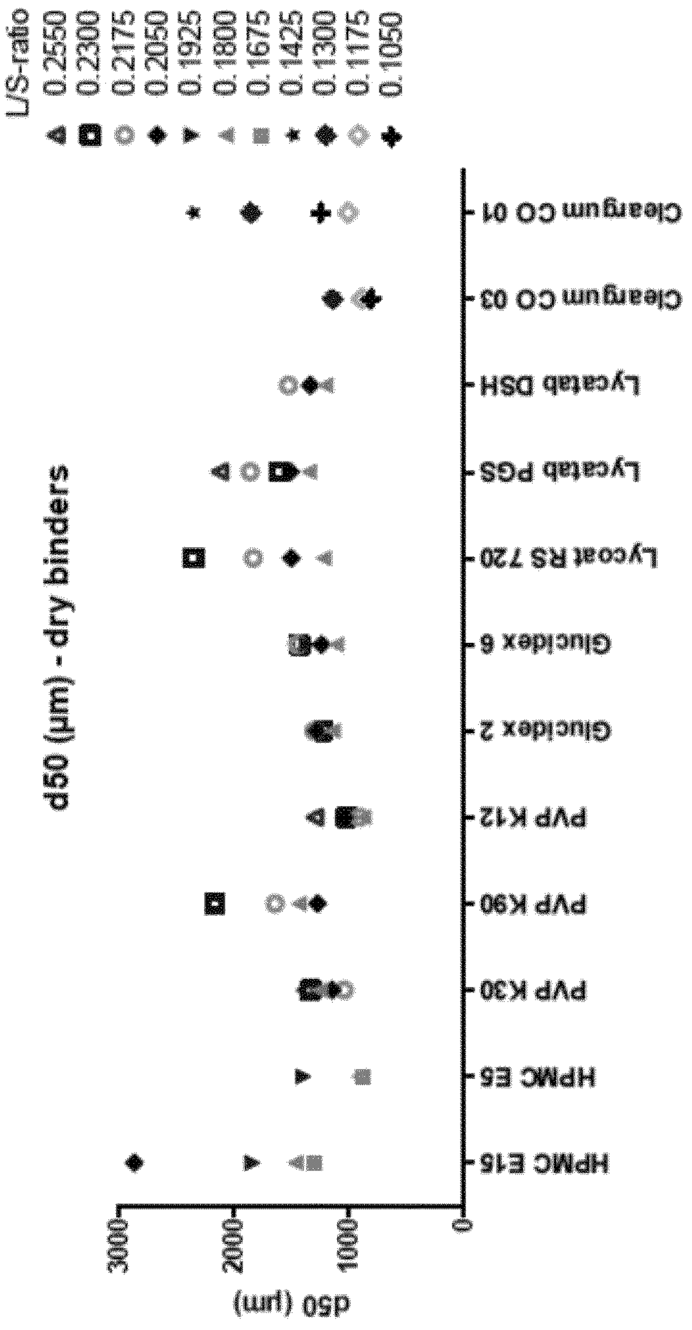
FIG. 1: Median particle sizes of the granules produced with the dry binders as a function of L/S ratio.

The inventors evaluated the binder effectiveness of different modified starches types and conventional binders in continuous wet granulation. They demonstrated that starch, in particular sodium octenyl succinate starch required a lower amount of granulation liquid to yield good granule quality. This behavior is attributed to the wetting properties of the binder.

The present invention relates to a method for preparing granules comprising one or several substances by continuous wet granulation comprising the steps of:

a) feeding substances powder to a continuous wet granulator;
b) feeding a granulation liquid to said granulator,
c) wetting the substance powder with the granulation liquid in presence of a binder comprising an octenyl succinate starch in order to obtain granules,
d) drying said granules.

The term "granule" refers to an agglomerate made of primary particles. The granules can be obtained by different methods in particular granulation. The granules can be obtained by wet granulation where agranulation liquid is used to agglomerate powders. The unmilled granules may have any suitable size, preferably in the range from 0.1 to 2 mm.

The term "substances" refers to any compounds of interest. The particular nature of the compound is not critical and any substance may be employed. In a particular embodiment, said substance is an active substance.

The active substance employed herein comprises non-pharmaceutical and pharmaceutical agent. The term "active" is typically used to refer to any substance of interest, for example, pharmaceutical, veterinary, food, nutraceutical, cosmetic or agrochemical. Examples of such active substances are pharmaceutical active ingredients, colorants, flavours. Preferably, the active substance of the invention is a pharmaceutical active agent, preferably intended for humans. The pharmaceutical active agent, may be chemical molecules, but also so-called "biological" active ingredients, as is the case for example with active substance based on or derived from proteins, nucleic acids—such as those derived from DNA or RNA—cells or viruses.

The substances can be initially milled in order to produce a uniform distribution of the substances referring as substances powder. The substances can also be directly purchased in powder form.

The substances powder can be homogenized with excipients powder. Said excipient is selected to ensure the delivery of a consistent amount of substances, in particular active substances in a convenient unit dosage form and to optimize the cost, ease and reliability of the manufacturing process. The excipients can be fillers (or diluents), disintegrants, lubricants, anti-adherents, glidants, wetting and surface active agents, stabilizers, pigments, flavoring agents, sweeteners, adsorbents, and taste-maskers.

The binder according to the invention is octenyl succinate starch, preferably sodium octenyl succinate starch.

The binder is a critical formulation component with appropriate surface wetting to ensure adhesion and cohesion between substance powders in granules in wet granulation process. The binder according to the disclosure has a high surface wettability. In a preferred embodiment, the binder solution (8% w/w) has a contact angle of less than 45°, preferably 40° with anhydrous dicalcium phosphate (CAS No. 7757-93-9) compacted at a pressure of 20 kN, preferably with a 10 mm diameter punch when said binder touches the surface of anhydrous dicalcium phosphate. In particular, said surface contact angle is preferably measured as described in examples of the present disclosure.

The octenyl succinate starch of the disclosure is a starchy material. The expression "starchy material" classically refers to a substance obtained from starch. It is reminded that the expression "starch" classically refers to the starch isolated from any suitable botanical source such as maize, tapioca barley by any technique well known to those skilled in the art. Isolated starch typically contains no more than 3% of impurities; said percentage being expressed in dry weight of impurities with respect to the total dry weight of isolated starch. These impurities typically comprise proteins, colloidal matters and fibrous residues. Suitable botanical source includes for instance legumes, cereals, and tubers.

Octenyl succinate starches are well known to those skilled in the art. Octenyl succinate starches are typically obtainable by esterification, for instance from the reaction of a starchy material with octenyl succinic anhydride.

In a preferred embodiment, the octenyl succinate starch according to the disclosure is further partially hydrolyzed, preferably with alpha-amylase.

In a preferred embodiment, the octenyl succinate starch according to the disclosure is derived from starch comprising more than 50% of amylopectin, expressed as dry weight relative to the total dry weight of said starch. This amylopectin content can be classically determined by the person skilled in the art by way of potentiometric analysis of iodine absorbed by amylose to form a complex. In a preferred embodiment, the octenyl succinate starch according to the disclosure is derived from starch exhibiting an amylopectin content of at least 60%, still preferably of at least 80%, still preferably of at least 90%, still preferably of at least 95%.

In a preferred embodiment, the octenyl succinate starch according to the disclosure is derived from waxy starch, even more preferably from waxy maize starch.

In a preferred embodiment, the octenyl succinate starch according to the disclosure is sodium octenyl succinate starch.

In a preferred embodiment, the octenyl succinate starch according to the disclosure has a critical aggregation concentration, selected within the range of from 1% to 10%, preferably selected within the range of from 1.5% to 5%.

The critical aggregation concentration has been determined by measuring the surface tension ($\gamma_{LV}$, mN/m) of the binder at different concentrations using tensiometer KRÜSS K12 with Wilhelmy plate. In a logarithmic representation of the surface tension versus the binder concentration there are two linear regimes below and above the critical aggregation concentration. The critical aggregation concentration corresponds to the point on the curve of the surface tension related to binder concentrations at which a sharp change of slope occurs. An extrapolation of respective regression lines yields the critical aggregation concentration at the intersection.

In a preferred embodiment, the octenyl succinate starch according to the disclosure has a Brookfield viscosity selected within the range of from 10 to 1000 mPa·s; said viscosity being determined on a solution comprising 24% dry weight of said octenyl succinate starch with respect to the total weight of the solution, at 20° C., after 20 min at 60 rpm using a spindle No. 1. of Brookfield viscometer RVT.

More preferably, this viscosity is selected within the range of from 20 to 300 mPa·s, still preferably 50 to 150 mPa·s.

The octenyl succinate starch according to the disclosure might undergo other chemical and/or physical modification than the preferred ones exposed before, as long as it does not interfere with the desired properties, notably in term of safety and efficiency of the final powder.

However, and because it appears that it is not necessary in the present invention, the octenyl succinate starch of the invention is preferably no further modified.

As example of suitable octenyl succinate starch commercially available, mention may be made of the one marketed under the name CLEARGUM® CO01, CLEARGUM®COA1 or CLEARGUM® CO03 (ROQUETTE). In a preferred embodiment, CLEARGUM®CO01 has a Brookfield viscosity selected within the range from 90 to 200 mPa·s, and CLEARGUM®CO03 has a Brookfield viscosity selected within the range from 20 to 100 mPa·s.

The use of octenyl succinate with weight average molecular weight (Mw) comprised between $10^4$ and $10^7$ g/mol, preferably $10^4$ and $10^6$ g/mol, more preferably $10^5$ and $10^6$ g/mol as binder yield to good granule quality with only low amount of granulation liquid.

According to the invention, said octenyl succinate starch has a weight average molecular weight comprised between $10^4$ and $10^7$ g/mol, preferably $10^4$ and $10^6$ g/mol, more preferably $10^5$ and $10^6$ g/mol. In a first preferred embodiment, said octenyl succinate has a weight average molecular weight of between 100 000 and 500 000 g/mol, preferably 100 000 and 400 000 g/mol, still preferably 100 000 and 300 000 g/mol, still preferably 100 000 and 200 000 g/mol, still again more preferably 150 000 g/mol. In another preferred embodiment, said octenyl succinate has a weight average molecular weight comprised between 300 000 and $10^6$ g/mol, more preferably 400 000 to 900 000 g/mol, still preferably 500 000 to 800 000 g/mol, still preferably 550 000 to 750 000 g/mol, more preferably 600 000 g/mol.

In a preferred embodiment, said octenyl succinate is CLEARGUM® CO 03 (CAS N°66829-29-6; Roquette), CLEARGUM® CO 01 (CAS N°66829-29-6) or CLEARGUM® CO A1 (CAS N°52906-93-1).

The weight average molecular weight can be determined by the person skilled in the art by dissolving the sample in elution solvent consisting of aqueous 0.1 mol/L sodium nitrate (Merck ref.: 6546) solution containing 0.02% sodium azide (Aldrich ref 19.993-1) filtered on a 0.02 micron filter (degassed HPLC-grade water) and analyzed with size exclusion chromatography, equipped with a MALS-Detector. The MW—distribution is recorded, the mean value of the complete weight distribution is calculated. As a non-limiting example, the high performance liquid chromatography unit is equipped with a high pressure isocratic pump (WATERS 515 type), an autosampler (WATER 717+ type), a differential refractometer (WATERS 2414-type), a column oven, a multi-angle static light scattering (MALS)-Detector (DAWN HELEOS II (WYATT)). In a preferred embodiment, the analysis is realized with an injected volume of 100 µL and a mobile phase output of 0.5 mL/min, a temperature of 40° C. during 110 minutes. A normalization step is performed by preparing a normalization sample by adding 10 mL of elution solvent to 40 mg of Pullulan P50 Shadex standard kit P82 (Waters-ref. WATO34207) and incubating during 30 min at 100° C. with low stirring. 100 µL of the resulting solution is analyzed with said size exclusion chromatography. The sample is then prepared by adding 10 mL of elution solvent to 100 mg of the sample and incubating during 30 min at 100° C. and analyzed with said size exclusion chromatography. The molecular weight is calculated with Astra software.

In a particular embodiment, said octenyl succinate starch is present at a concentration comprised between 1 and 50%, preferably 1 and 10%, more preferably 5% by dry weight of the total dry weight of said granules.

In a preferred embodiment, the substances are granulated using dry addition method of the binders. In this particular embodiment, the binder consisting of octenyl succinate starch as previously disclosed in powder form is mixed with substance powder. The resulting powder mixture is then fed in a continuous granulator. Granulation liquid is fed in said continuous granulator. In this case, the granulation liquid is a solvent, preferably selected from the group consisting of water, organic solvents such as ethanol, isopropanol, methanol, acetone and a mixture thereof, preferably a mixture comprising at least 50% of water, more preferably said granulation liquid is water. Said granulation liquid must be volatile to be easily removed by drying. The powder mixture is wetted with the granulation liquid in order to obtain granules. Thus, in the case of dry addition of the binders, the substances powder is mixed with binder powder prior to be fed in the continuous wet granulator. The granulation liquid is afterwards fed in the barrel of the continuous granulator. The substances and binder powder mixture are then wetted with the granulation liquid.

In another particular embodiment, the substances are granulated using wet addition of the binders. In this particular method, the substances powder is fed in the continuous wet granulator. The granulation liquid which comprises the binder consisting of octenyl succinate starch as previously described is fed in said continuous wet granulator. The substance powder is then wetted with granulation liquid comprising the binder.

In this particular embodiment, said granulation liquid comprising said binder is prepared by dissolving octenyl succinate starch as previously described in a solvent. Said solvent must be volatile to be easily removed by drying. Preferably, said solvent is selected from the group consisting of ethanol, water, isopropanol, methanol, acetone and a mixture thereof, preferably a mixture comprising at least 50% of water, more preferably said solvent is water.

In a preferred embodiment, the granulation liquid comprising said octenyl succinate starch has a Brookfield viscosity at 25° C. comprised between 50 and 300 mPa·s$^{-1}$, preferably 50 and 150 mPa·s$^{-1}$, more preferably 74 mPa·s Viscosity was measured with a Brookfield Digital Viscometer DV-I with a rotation speed was 100 rpm.

Said granulation is realized in a continuous wet granulator. A continuous wet granulator is able to combine wet granulation process steps in one equipment; preferably powder undergoes, nucleation and wetting, consolidation and breakage and attrition along the length of the granulator barrel. In particular said granulation is performed in 5 to 20 seconds. Said granulator is preferably an extruder without a die placed at the end of the barrel.

In a preferred embodiment, said granulation is realized in a twin-screw granulator. Generally, a twin-screw granulator comprises two co-rotating screws inside a closed barrel, which is divided in different parts, in particular the feeding zone, two transition zones containing conveying and mixing zones. The powder mixture is fed through the feeder and passed through the barrel having various mixing and conveying zones. The agglomeration occurs after the addition of the granulation liquid to the barrel of the granulator. Conveying zones transport the material whereas in the kneading zones densification of the material occurs.

In a more preferred embodiment, said twin-screw granulation is performed at a screw speed comprised between 100 to 1500 rpm, 200 to 900 rpm.

In another preferred embodiment said twin-screw granulation is performed at a throughput comprised between 5 and 20 kg/h.

In another particular embodiment, said continuous wet granulation is performed at a temperature of 4 to 100° C., preferably 30° C.

Finally, the granules may be dried using common techniques known by a person skilled in the art with appropriate moisture content, preferably a loss-on-drying value between 0 to 20% by weight of water, more preferably 1 and 3% by weight of water.

Drying is preferably conducted at a temperature comprised between 20 and 120° C., preferably 60° C. during 10 to 180 minutes in a fluid bed. The water content is measured using the Sartorius moisture analyzer MA150 at a drying temperature of 120° C. with the automatic mode.

Then, the dried granules can be submitted to a milling step to obtain an appropriate particle size distribution for the subsequent processes, preferably granule size in a range from 150 to 1400 μm measured by dynamic image analysis. The sizing step is preferably achieved using a low shear screening mill, such as U5 Comil.

The dried granules can then be prepared in a solid dosage form, for example for oral administration. Solid dosage forms include tablets, capsules, pills, troches, cachets, and the like.

Thus, the present disclosure also relates to a method for preparing pharmaceutical tablet wherein the resulting granules obtained by the method as previously described are compressed into a tablet. In another embodiment, the granules are enclosed in a capsule.

Lubricant can be added before compression step to facilitate tablet ejection. As used herein, the term "lubricant" refers to any pharmaceutically acceptable agent which reduces surface friction, lubricates the surface of the granule, decreases tendency to build-up of static electricity, and/or reduces friability of the granules. Preferably, said lubricant is a magnesium stearate.

Preferably, the compression step is performed by way of a tablet press, for instance by way of a single-punch press or rotary tablet press, preferably by way of a rotary tablet press Preferably, the compression step is realised with a machinery which typically contains two steel punches within a steel die cavity. The tablet is formed when pressure is exerted on the dried granules by the punches in the cavity.

The present disclosure also relates to a granule obtainable by the method for preparing granules as previously described. Said granule comprises one or several substances and a binder as previously described.

In another aspect, the present invention relates to a pharmaceutical tablet obtainable by the method for preparing the tablet as previously described. Said pharmaceutical tablet comprises a granule as previously described. In another embodiment said pharmaceutical tablet comprises one or several substances and a binder as previously described.

Preferably, the pharmaceutical tablet according to the invention has friability lower than 5%, preferably lower than 2%, more preferably from 5 to 1%. The friability might be determined by the person skilled in the art by using a friabilator described in Eur. Ph. (PTF E Pharma Test, Hainburg, Germany), at a speed of 25 rpm for 4 min. The percentage weight loss was expressed as the tablet friability.

Other characteristics and advantages of the present invention will emerge clearly on reading the examples given hereinafter, which illustrate the invention without however limiting it.

EXAMPLES

1. Friability and Particle Size of the Granules

Granulation experiments were performed using the twin screw granulator of a continuous from-powder-to-table-line (ConsiGma™-25 system, GEA Pharma Systems).

The powder is fed through the feeder at a feeder rate was 20 kg/h.

The twin screw configuration exists of two blocks of 6 kneading elements, stagger angle 60° separated with conveying elements (1.5 L/D). Another configuration was tested with the last kneading element of each kneading zone staggered at an angle of 90°. The processing temperature is at 30° C. and the screw speed is 300 rpm.

Anhydrous dicalcium phosphate (DCP) was granulated using both dry (as dry powder in the preblend) and wet (as an aqueous solution) addition of the binders. The concentration of the dry binders was 5% by dry weight of the total dry weight of said powder mixtures. Via wet addition, the concentration of the binders in the granules was 1.44% by dry weight of the total dry weight of said granules. In addition, depending on the viscosity of the binder solution, higher concentrations (3 and/or 5%) could be achieved for specific binders. The addition method (wet and dry) and the effect of the different binders (cleargum CO 01 (600 000 g/mol), cleargum CO 03 (150 000 g/mol), Glucidex 2, Glucides 6, HPMC E5, HPMC E15, Lycatab DSH, Lycatab PGS, Lycoat RS720, PVP K12, PVP K30 and PVP K90) was evaluated on the granule properties (granule friability and particle size distribution). The granule friability was determined using a friabilator (PTFE Pharmatest) equipped with an abrasion drum. The particle size of the granules was analyzed by dynamic image analysis using a QICPIC particle size analyser (Sympatec, Germany).

Generally, water or liquid content is expressed as liquid to solid ratio (L/S). The liquid-to-solid (L/S) ratio was varied from 0.105 to 0.225. The granules were tray-dried until a loss-on-drying between 1 and 3% by weight was obtained.

Dry Addition Method

Dry addition method using a fixed binder concentration of 5%, the particle size distribution was significantly influenced by the L/S-ratio as a higher L/S-ratio resulted in larger granules. Cleargum CO 01 produced granules with an extremely large median particle size (d50) (4026 μm) at low L/S-ratio (0.155) compared to the other binders, which can be attributed to the amphiphilic properties of this binder. The d50 values of the obtained granules with the dry added binders are illustrated in FIG. 1.

Figure 2:
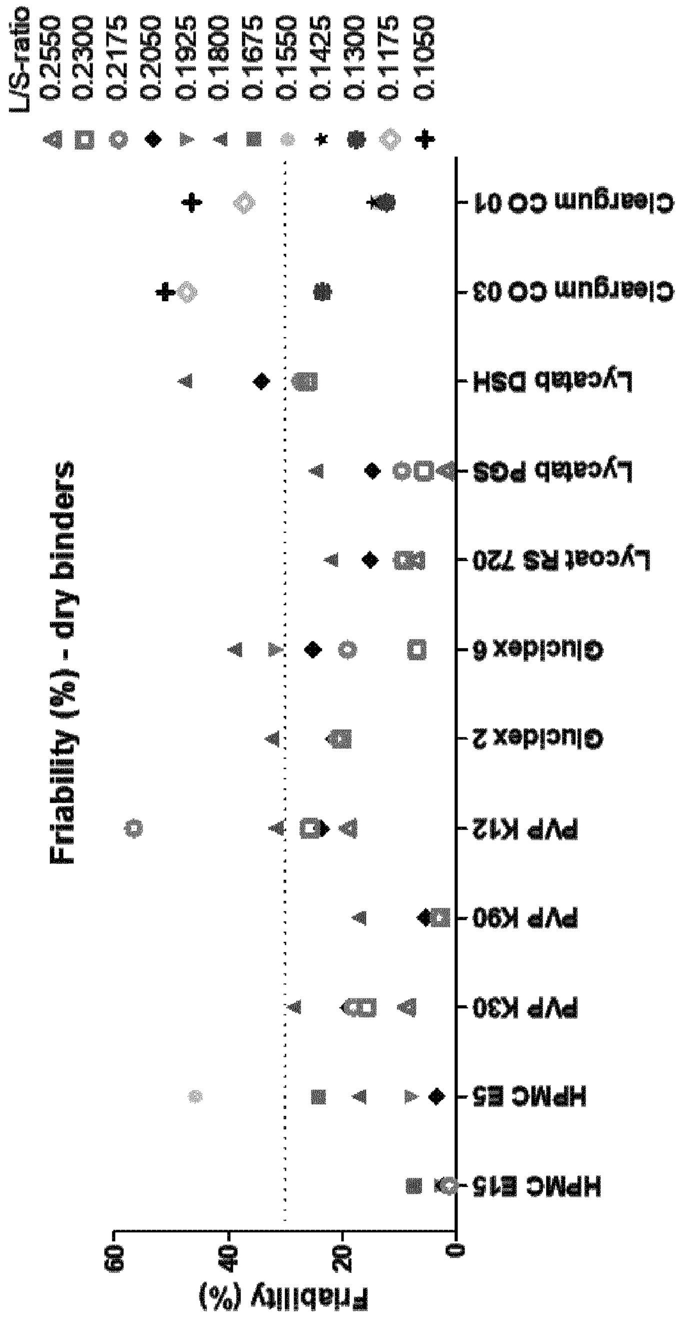
FIG. 2: Friability of the granules produced with the dry binders as a function of L/S ratio.

The L/S-ratio also strongly affected the friability since a higher L/S-ratio resulted in less friable granules for each binder. If a higher amount of granulation liquid is added, a larger fraction of the binder is able to contribute to the interaction as more binder is in contact with the fluid. The friability of the granules produced with dry binders is illustrated in FIG. 2.

As Cleargum is processable at lower L/S-ratios, less water is needed to activate the binder properties of this binder. Therefore, it can be said that the intrinsic binder capacities of Cleargum in a continuous process are considered to be higher when compared to other binders which need more liquid. The friability of the resulting granules is low (<30%).

Wet Addition Method

The granule size distribution of the wet added binders depended on both the L/S-ratio and the binder content in the dried granule. Larger granules were produced with a higher L/S-ratio and a higher binder concentration in the dried granule. However, when operating at the highest L/S-ratio of Cleargum CO 03, overwetted granules with a particularly high median particle size were observed (>10000 μm).

Remarkably, the L/S-ratio range in which Cleargum CO 03 and Cleargum CO 01 could be processed was lower compared to the other binders, indicating that less granulation liquid is needed for activation of these binders.

2. Characterisation of the Binder: Wettability of the Binders

Wettability of the binders was determined via surface contact angle measurements using a Drop Shape Analyzer (DSA 30, KRÜSS GmbH, Hamburg, Germany) applying the sessile drop method. Two different types of experiments were performed. (i) anhydrous dicalcium phosphate (DCP) (Calipharm® A, obtained from Innophos, Chicago Heights, USA) was compressed with a compaction simulator (Styl'One Evolution, Medelpharm, Lyon, France) at a pressure of 20 kN with a 10 mm diameter punch. As tableting of pure DCP resulted in high ejection forces, no high forces could be applied. This resulted in high tablet porosity. Aqueous binders dispersions were prepared (8% w/w) and 5 μl of each dispersion was placed on the DCP tablet. Contact angles (°) were measured when the drop touched the surface of the tablet (CADCP). Due to high porosity, no angle at 30 s could be obtained. Five replicate measurements were performed. (ii) A droplet of each binder dispersion (8% w/w) was also placed on a polytetrafluoroethylene (PFTE) surface. As PFTE is an inert substance, no differences in angles were seen over time. Contact angles (°) were therefore only measured when the drop touched the surface (CAPFTE). Measurements were performed in triplicate.

TABLE 1

Contact angles (°) of the different binders measured when the drop touched the surface of CADCP and CAPFTE.

| | Contact angle (°) | |
|---|---|---|
| | CAPFTE | CADCP |
| PVP K12 | 96.3667 | 109.6 |
| PVP K30 | 101.867 | 81.3 |
| PVP K90 | 98.2 | 84.73 |
| HPMC E5 | 83.7667 | 90.8 |
| HPMC E15 | 82.13 | 69.63 |
| PVA 4-88 | 82.9333 | 36.77 |
| Maltodextrin 2 | 100.067 | 113.8 |
| Maltodextrin 6 | 95.37 | 103 |
| Starch octenyl succinate | 77.9667 | 32.8 |
| HP pea starch | 94.9333 | 95.27 |
| Maltodextrin DSH | 99.2 | 101.05 |

The wetting of the hydrophobic polytetrafluoroethylene (PFTE) surfaces with starch octenyl succinate solution resulted in the lowest contact angle. The starch octenyl succinate presents therefore good wetting properties of PFTE (Table 1).

These values are confirmed by using a concrete model, based on densified anhydrous dicalcium phosphate tablets (CADCP). The inventors find significant differences between all tested binders. Binders with Starch octenyl succinate presents a contact angle of 32.8° (Table 1).

Dry and wet binder characterization showed that Cleargum has particular wetting behaviour. A low contact angle was observed when a Cleargum solution (starch octenyl succinate) was measured against DCP. This can declare the processability at lower L/S-ratios when compared to other binders.

3. Characterization of Tablets

Mannitol was granulated using dry addition of the binders. The concentration of the dry binders was 5% by dry weight of the total dry weight of said powder mixtures. The milled granules were blended with 1.2% w/w magnesium stearate in a tumbling blender (T2F, W.A. Bachofen, Basel, Switzerland) before tableting. Tablets were prepared using a Styl'One compaction simulator equipped with a 10 mm punch. Tablets were compressed at 5 different main compression forces: 5, 10, 15, 20, 25 kN and were tested for disintegration time in 900 ml of demineralized water of 37±0.1° C. with n=5 (PharmaTest, Hainburg, Germany). Hardness of the tablets (n=5) was also determined using a hardness tester (Type HT 10, Sotax, Basel, Switzerland).

Figure 3:
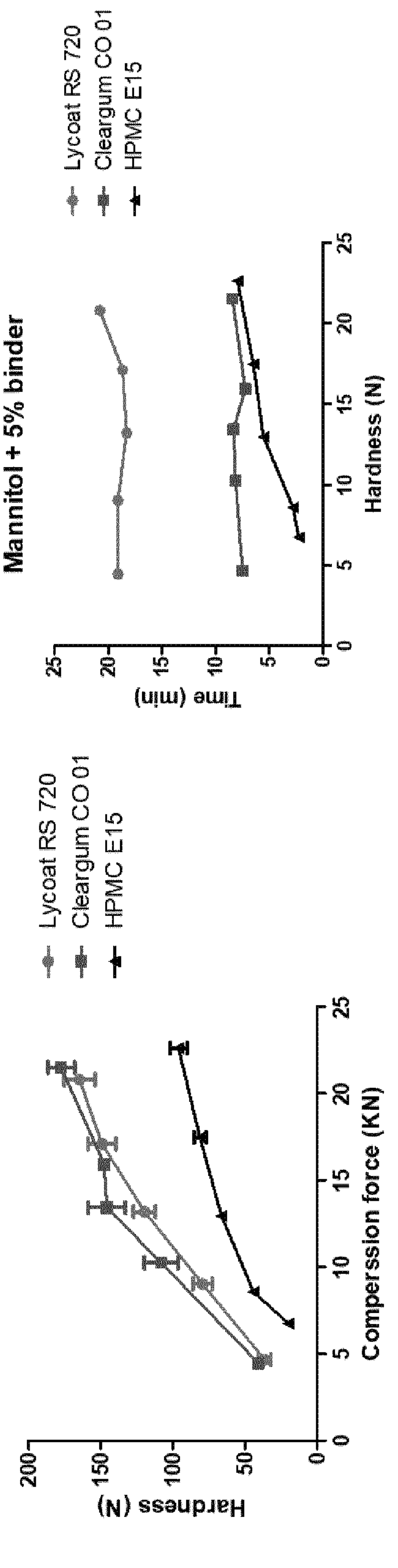
FIG. 3: Hardness and time of disintegration of tablets obtained with different binders.

Tablets of Mannitol granulated with Cleargum CO 01 present a high hardness and a low time of disintegration (FIG. 3).

CONCLUSION

The effect of different binder types and the addition method was evaluated on the quality of granules produced via twin screw granulation. This study demonstrated that different binder types and the addition methods affected granule properties differently. From an industrial point of view, dry addition of binders is preferred because of its ease of manufacturing.

Cleargum CO 01 and Cleargum CO 03 binders required a lower L/S ratios to produce good granule quality. The need for a lower amount of granulation liquid to obtain good granule quality is beneficial for granule drying. The lower L/S-ratio can be explained by the efficient wetting of the powder bed by these binders.

The invention claimed is:

1. A method for preparing granules comprising one or several powder substances by continuous wet granulation, the method comprising the steps of:

a) feeding the one or more powder substances to a continuous wet granulator;

b) feeding a granulation liquid to said continuous wet granulator, c) wetting the powder substances with the granulation liquid in presence of a binder consisting of a partially hydrolyzed waxy octenyl succinate starch in order to obtain said granules and d) drying said granules, wherein said continuous wet granulation is extrusion granulation, and wherein said partially hydrolyzed waxy octenyl succinate starch has a weight average molecular weight from $10^5$ to $10^6$ g/mol, wherein said partially hydrolyzed waxy octenyl succinate starch is present in an amount of from 1 to 15% by weight, based on the total dry weight of said granules.

2. The method of claim 1 wherein said continuous wet granulation is twin screw granulation.

3. The method of claim 1 comprising the steps of:
a1) mixing the one or several powder substances with powder of said binder,
a2) feeding said powder mixture to a continuous wet granulator,
b) feeding a granulation liquid consisting of a solvent to said continuous wet granulator,
c) wetting the powder mixture with the solvent in order to obtain said granules,
d) drying said granules.

4. The method of claim 1 comprising the steps of:
a) feeding said one or several powder substances to a continuous wet granulator,
b) feeding a granulation liquid comprising said binder to said continuous wet granulator,
c) wetting the one or several powder substances with the granulation liquid in order to obtain said granules,
d) drying said granules.

5. The method of claim 1, wherein said partially hydrolyzed waxy octenyl succinate starch has a weight average molecular weight of from 100,000 to 500,000 g/mol.

6. The method of claim 1, wherein said partially hydrolyzed waxy octenyl succinate starch has a weight average molecular weight of from 300,000 to $10^6$ g/mol.

7. The method according to claim 1 further comprising a step e) of milling the dried granules.

8. The method according to claim 1 wherein said partially hydrolyzed waxy octenyl succinate starch is a waxy maize octenyl succinate starch.

9. The method according to claim 1 wherein said one or more powder substances include a pharmaceutical active agent.

10. A method for preparing pharmaceutical tablets comprising the steps of preparing granules according to claim 1 and a final step of compressing the granules in order to obtain tablets.

11. A continuous wet granulation method, comprising the step of incorporating a binder comprising partially hydrolyzed waxy octenyl succinate starch, wherein said continuous wet granulation is extrusion granulation, and wherein said partially hydrolyzed octenyl succinate starch has a weight average molecular weight of from $10^4$ to $10^5$ g/mol, wherein said partially hydrolyzed waxy octenyl succinate starch is present in an amount of from 1 to 15% by weight, based on the total dry weight of said granules.

* * * * *